United States Patent [19]

Roeschert et al.

[11] Patent Number: 5,328,973
[45] Date of Patent: Jul. 12, 1994

[54] RADIATION-SENSITIVE MIXTURE WITH A POLYMERIC BINDER CONTAINING UNITS OF α,β-UNSATURATED CARBOXAMIDES

[75] Inventors: Horst Roeschert, Ober-Hilbersheim; Georg Pawlowski, Wiesbaden; Klaus-Juergen Przybilla, Frankfurt am Main, all of Fed. Rep. of Germany

[73] Assignee: Hoechst Aktiengesellschaft, Frankfurt am Main, Fed. Rep. of Germany

[21] Appl. No.: 922,507

[22] Filed: Jul. 31, 1992

[30] Foreign Application Priority Data

Aug. 9, 1991 [DE] Fed. Rep. of Germany ....... 4126409

[51] Int. Cl.$^5$ ............... C08F 20/60; C08F 24/00; C08F 30/08
[52] U.S. Cl. ................... 526/262; 526/266; 526/270; 526/279; 526/304; 526/292.9; 526/292.95; 526/298; 430/906; 430/910; 430/270
[58] Field of Search ............. 526/304, 292.2, 292.95, 526/262, 266, 270, 279; 430/906, 910, 270

[56] References Cited

U.S. PATENT DOCUMENTS 4,491,628  1/1985  Ito et al. ................. 430/176
4,689,288  8/1987  Buiguez et al. ............ 430/270
4,770,977  9/1988  Buiguez et al. ............ 430/323
5,068,163  11/1991 Elsaesser et al. .......... 430/192
5,120,629  6/1992  Bauer et al. .............. 430/70
5,130,392  7/1992  Schwalm et al. ........... 526/288

OTHER PUBLICATIONS

T. W. Greene, "Protective Groups in Organic Chemistry" Wiley, New York, 1981, pp. 21-24, 94-98.
Ito "Solid-State Thermolysis of Poly(p-t-Butoxycarbonyloxystyrene) Catalyzed by Polymeric Phenol: Effect of Phase Separation", *Journal of Polymer Science: Part A Polymer Chemistry Ed.*, 24:2971-2980, (1986).
Crivello "Applications of Photoinitiated Cationic Polymerization Toward the Development of New Photoresists" *Org. Coatings and Appl. Polym. Sci.*, 48:pp. 65-69, (1985).

*Primary Examiner*—Mark Nagumo
*Attorney, Agent, or Firm*—Foley & Lardner

[57] ABSTRACT

A radiation-sensitive mixture which contains a polymeric binder having acid-labile side groups and a compound which generates a strong acid on irradiation wherein the binder is a polymer built up from novel amides of α,β-unsaturated carboxylic acids, is highly sensitive in the shortwave uv region and useful in the production of recording material.

21 Claims, No Drawings

RADIATION-SENSITIVE MIXTURE WITH A POLYMERIC BINDER CONTAINING UNITS OF α,β-UNSATURATED CARBOXAMIDES

BACKGROUND OF THE INVENTION

1. Field of the Invention

The invention relates to a radiation-sensitive mixture which contains a polymeric binder having acid-labile side groups and a compound which generates a strong acid on irradiation.

In addition, the invention relates to α,β-unsaturated carboxamides with which the polymers used as binders can be prepared and to the polymers so prepared.

2. Description of the Related Art

A frequently used positive-working radiation-sensitive mixture for producing radiation-sensitive recording materials contains an o-quinonediazide derivative and a binder which is soluble in aqueous-alkaline solvents, for example a novolak or a polyhydroxystyrene binder. However, the sensitivity of these systems to radiation, in particular shortwave radiation, is sometimes unsatisfactory. Due to their high intrinsic absorption, novolaks are unsuitable as binders in an insert resist material for deep UV lithography (220-330 nm). By contrast, polyhydroxystyrenes have more favorable absorption properties and are additionally distinguished by a better heat holdout. However, polymers of this type are accessible only by involved multi-stage syntheses. The lithographic properties of polymers composed of unsubstituted hydroxystyrene are unsatisfactory because of their unbalanced hydrophilic/hydrophobic character both in 3-component systems and in 2-component systems. There is therefore a need for binders for highly resolving, highly sensitive resist materials which have good transparency even in the UV-2 region and a high heat holdout, and which can be developed under aqueous-alkaline conditions.

Mixtures which exploit the principle of the so-called "chemical intensification" i.e. which contain, in addition to an acid-cleavable compound, a compound which releases a catalytically acting acid under the action of radiation, generally show a higher radiation sensitivity. Examples of the acid-generating compounds are diazonium, phosphonium, sulfonium and iodonium salts, nitrobenzyl esters, phenolic methanesulfonates, diazo compounds and halogen compounds. The use of onium salts as photochemical acid generators in resist materials is known, for example, from U.S. Pat. No. 4,491,628. A review of the use of onium salts in resist materials is given by Crivello in Org. Coatings and Appl. Polym. Sci., 48, pages 65-69 (1985).

Radiation-sensitive mixtures of polymers with acid-labile side groups and photochemical acid generators are known from U.S. Pat. No. 4,491,628 and FR-A 2,570,844. However, only polymers of para-substituted styrene or α-alkylstyrene are completely disclosed in these two publications. Only tert.-butoxycarbonyloxy groups and trialkylsilanyloxy groups are listed as acid-labile para-substituents. The polymeric binders with the acid-labile side groups are extremely hydrophohic. The acid generated on exposure effects elimination of the acid-labile protective groups and thus causes the polymeric binders to become soluble in alkali.

Copolymers having acid-labile groups bound via a phenolic oxygen atom, for example copolymers of p-hydroxystyrene and p-(tert.-butoxycarbonyloxy)styrene, are known from J. Poly. Sci., Part A, Polym. Chem. Ed., 24:2971-2980 (1986).

The polymers described in German Patent Application P 4,120,172.8 show a marked improvement of the transparency properties in the desired wavelength region. It is achieved, however, only by introducing a high proportion of acid-labile protective groups, whereby the hydrophobic/hydrophilic balance is, adversely affected. Moreover, there are as a rule adhesion problems in systems which contain highly hydrophobic binders.

SUMMARY OF THE INVENTION

Accordingly, it is an object of the present invention to provide a novel mixture, which is highly radiation-sensitive in the shortwave UV region, for the production of relief structures, which mixture can be developed by aqueous-alkaline solutions.

It is further an object of the present invention to provide a polymeric binder with acid-cleavable side groups which is useful in a radiatin-sensitive mixture.

It is further an object of the present invention to provide a method of producing such a polymeric binder and furthermore to provide compounds which can be used to synthesize the polymeric binders.

In accomplishing the foregoing objectives, there has been provided, in accordance with one aspect of the present invention a compound of the formula II

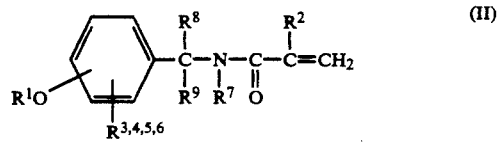

in which $R^1$ is an acid-labile protecting group, $R^2$ is ($C_1$-$C_4$)-alkyl, halogenated-($C_1$-$C_4$)-alkyl, halogen, CN, or hydrogen, $R^{3,4,5,6}$ independently of one another are aliphatic, araliphatic or aromatic radicals each independently having 1 to 20 carbon atoms and each being unsubstituted or halogen substituted, halogen, hydroxyl or hydrogen, $R^7$ is a hydrogen atom or a ($C_1$-$C_4$)-alkyl group, and $R^8$ and $R^9$ are identical or different and are hydrogen, a ($C_1$-$C_6$)-alkyl group or a ($C_6$-$C_{10}$)-aryl group.

In accordance with another aspect of the present invention there is provided a polymer containing repeat units of the formula I

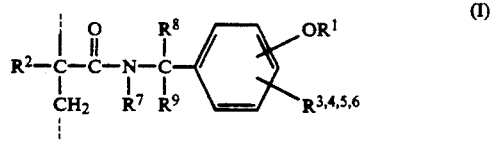

in which $R^1$ is an acid-labile protecting group, $R^2$ is ($C_1$-$C_4$)-alkyl, halogenated($C_1$-$C_4$)-alkyl, halogen, CN or hydrogen, $R^{3,4,5,6}$ independently of one another are an aliphatic, araliphatic or aromatic radical each independently having 1 to 20 carbon atoms and each being unsubstituted or halogen substituted, halogen, hydroxyl or hydrogen, $R^7$ is a hydrogen atom or a ($C_1$-$C_4$)-alkyl group, and $R^8$ and $R^9$ are identical or different and are hydrogen, a ($C_1$-$C_6$)-alkyl group or a ($C_6$-$C_{10}$)-aryl group.

In accordance with another aspect of the present invention there has been provided a radiation-sensitive mixture containing a photoactive compound which releases upon radiation an acid and as a binder a polymer of formula I.

In accordance with another aspect of the present invention there is provided a recording material which comprises a support and disposed thereon, a radiation-sensitive mixture as described above.

In accordance with another aspect of the present invention there is provided a method of producing relief patterns comprising the steps of a) applying a 0.1 to 5 micron thick layer of the radiation-sensitive mixture to a substrate, so as to form a radiation-sensitive layer on the substrate, b) imagewise exposing the layer through a mask, c) optionally heating the exposed layer at a temperature of up to 150° C., d) developing the exposed layer so as to form developed resist structures, and e) optionally post-hardening the resist structures so as to crosslink said resist structures.

Further objects, features and advantages of the present invention will become apparent from the detailed description of preferred embodiments that follows.

DETAILED DESCRIPTION OF THE PREFERRED EMBODIMENTS

As compared with the known mixtures containing poly(4-hydroxystyrene), novolaks or polymers with units of esters of $\alpha,\beta$-unsaturated carboxylic acids as binders, the radiation sensitive mixtures according to the invention have the following advantages:

a) the monomeric $\alpha,\beta$-unsaturated carboxamides can be prepared in good yield by proven processes (such as described in EP-A 0,347,660) from inexpensive starting materials, b) two synthesis routes are available for the synthesis of the $\alpha,\beta$-unsaturated carboxamides, which has process engineering advantages, c) the heat holdout of the polymers according to the invention is substantially higher than that of polymers of the corresponding esters, due to the nature of the amide bond and the hydrogen bonds resulting therefrom, d) easy accessibility of the protected monomers, e) stability of the unprotected monomers, f) homopolymers and copolymers of high molecular weights can be prepared from the protected and also from the unprotected monomers, g) good transparency in the wavelength range between 220 and 300 nm, h) balanced hydrophilic/hydrophobic character and i) good adhesion properties.

Polymers with units of the formula I can in principle be prepared by two different routes. On the one hand, so-called "protected" monomers of the formula II

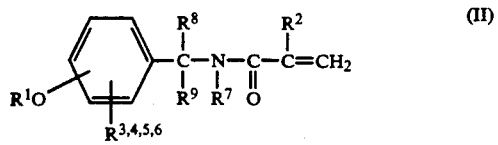

in which $R^1$ to $R^9$ have the definition given above can be polymerized either alone or with other polymerizable monomers. These monomers are novel and are a part of the present invention. Suitable acid-cleavable groups $R^1$ are any known in the art and are especially benzyl, trialkylsilanyl, alkoxycarbonyl (for example tert.-butoxycarbonyl, isopropoxycarbonyl and pentyloxycarbonyl), benzyloxycarbonyl, tetrahydropyranyl and tetrahydrofuranyl.

Those monomers of the formula II are particularly preferred in which $R^1$ is a benzyl, trialkylsilanyl, alkoxycarbonyl, tetrahydropyranyl or tetrahydrofuranyl group, $R^2$ is hydrogen or a methyl group, $R^3$ to $R^6$ independently of one another are each hydrogen, a hydroxyl group or a methyl group, preferably not more than two of these radicals being methyl groups, and $R^7$ to $R^9$ are hydrogen.

The tert.-butoxycarbonyloxy group is very particularly preferred as the acid-labile group $OR^1$; the group $OR^1$ is preferably in the ortho- or para-position relative to the $-CR^8R^9$ group.

Particularly preferred monomers are derivatives, formed with acid-labile groups $R^1$ of N-(2- and 4-hydroxybenzyl)-(meth) acrylamide, such as N-(4-tert.-butoxycarbonyloxy-benzyl)-(meth)acrylamide, N-(2-tert.-butoxycarbonyloxy-benzyl)-(meth)acrylamide, N-(3,5-dimethyl-4-tert.-butoxycarbonyloxy-benzyl)(meth)acrylamide, N-(3-methyl-4-tert.-butoxycarbonyloxybenzyl)-(meth)acrylamide and N-(3-methyl-2-tert.-butoxycarbonyloxy-benzyl)-(meth)acrylamide. Mixtures of these monomers can also be polymerized.

On the other hand, the N-(hydroxybenzyl)-(meth)acrylamides can be polymerized, since these are stable in the monomeric form. Derivatives of the polymers can then be formed in a subsequent step, in order to introduce the groups $R^1$. However, this procedure is not preferred since it is not always possible to reproducibly form derivatives of the phenolic hydroxyl groups in the polymers. At the same time, it is unavoidable in the two-stage process that traces of the base used in the derivative-forming reaction remain in the product.

The present polymers are more advantageous with respect to preparation and utility than polymers based on 4-hydroxystyrene. Particularly, 4-hydroxystyrene is not stable in the free form whereas the instant monomers are stable. Moreover, it can be prepared only in low yields by a 4-stage synthesis. Only a protected 4-hydroxystyrene, such as 4-(tert.-butoxycarbonyloxy)styrene, can therefore be used as starting material for the polymerization. The latter is prepared via a Wittig reaction from 4-hydroxybenzaldehyde (see U.S. Pat. No. 4,491,628). Alternatively, a poly(4-hydroxystyrene) with suitable protective groups has been reacted. This preparation process has, however, the serious disadvantage that as a result of the process the binder is contaminated with metal ions and with base. The presence of bases is a disadvantage for systems working with photochemical intensification. A high metal ion contamination is even unacceptable for the production of semiconductors. Binders prepared by this process frequently show non-reproducible lithographic properties.

These disadvantages are overcome by the polymers according to the invention and the radiation-sensitive mixture according to the invention, prepared with these polymers.

The polymeric binders according to the invention can be either homopolymers, which exclusively contain units of the formula I, or copolymers which, in addition to these, also contain other units. If yet further units are present in the polymers, in addition to the units of the formula I, these are preferably derived from "unprotected" monomers and/or monomers protected in an acid-stable manner, of the formula II (in these "protected" monomers, $R^1$ is hydrogen or a radical which cannot be eliminated by acid). These polymers can, however, also contain units which are derived from other conventional vinyl monomers. Any known vinyl monomer can be used as comonomers, including esters or amides of (meth)acrylic acid, such as hydroxyethyl methacrylate (HEMA), and also methacrylic acid itself, hydroxypropyl methacrylate, methyl methacrylate, ethyl methacrylate, methacrylamide and hydroxyethylmethacrylamide, can in particular also act as such further monomers. The adhesion properties of the binder can be modified with the use of these monomers.

Mixtures having an enhanced plasma stability are obtained if silicon-containing monomers such as trialkyl-vinyl-silanes or trialkylsilanyl acrylates and methacrylates are additionally used in the preparation of the polymers.

Finally, copolymers with maleimide can also be used which show increased solubility in aqueous-alkaline solutions and have a higher transparency in the deep UV region. The same effect is also shown by copolymers with styrene, substituted styrene, with vinyl ethers, vinyl esters, vinylsilane compounds or (meth)acrylic acid esters. The polymers according to the invention preferably contain at least 10 mol % of units of the formula I. Their number average molecular weight $M_n$ is preferably between 2,000 and 100,000, more preferably between 5,000 and 40,000, g/mol. The polymer according to the present invention may be used in any desired utility and is preferably used in a radiation sensitive mixture or polymeric binder. The polymeric binder is in general present in the mixture according to the invention in any desired amount, with quantities of 45 to 99% by weight, more preferably 85 to 98 by weight, and most preferably 90%-97% by weight, relative to the total weight of the solids in the radiation-sensitive mixture being particularly preferred.

The mixture according to the invention furthermore contains at least one photoactive compound which releases on irradiation a strong acid which in turn cleaves the protective groups present in the binder and thereby has the effect that the solubility of the binder and hence also of the mixture in aqueous-alkaline solution is greatly increased. The mixture is particularly sensitive to UV radiation (220–400 nm), electron beams and X-rays, and as resist material is also outstandingly suitable for the production of printing plates.

The acid generators can in principle be all compounds which generate a strong acid on irradiation. Examples of particularly suitable acid generators are sulfonium salts of the formula $[(C_6H_5)_3S]^+X^-$, X being especially chloride, bromide, perchlorate, hexafluorophosphate, hexafluoroarsenate, hexafluoroantimonate, tetrafluoborate or a sulfonate, such as methanesulfonate, trifluoromethanesulfonate or toluene-4-sulfonate. Nitrobenzyl esters, bis-sulfonyldiazomethanes, 1,2,3-tris-(alkylsulfonyloxy- or arylsulfonyloxy)-benzene, 1-sulfonyloxy-2-pyridones and halogen compounds are also suitable. For irradiation with shortwave UV light, however, iodonium salts and especially sulfonium salts are preferred.

The acid generator is present in the mixture in any desired amount with a quantity of 1 to 40% by weight, preferably 2 to 15% by weight, relative to the total weight of the solids in the radiation-sensitive mixture, being particularly preferred.

The radiation-sensitive mixture according to the invention can additionally contain further conventional auxiliaries and additives, such as adhesion promoters, wetting agents, dyes and plasticizers.

As appropriate, small quantities of sensitizers can also be added to the mixture in order to sensitize the acid generator for radiation in the longer-wave Uv up to the visible region. Polycyclic aromatics, such as pyrene, perylene and various heteroaromatics, such as phenothiazine, are preferred for this purpose, but dyes acting as sensitizers can also be used.

The invention also relates to a recording material with a support and a layer containing the radiation-sensitive mixture according to the invention, and to a method of producing relief structures or of structuring wafers.

The radiation-sensitive mixture may be applied in any known manner to the support material, and is advantageously dissolved in an organic solvent, the solids content in general being in the range between 5 and 40% by weight to facilitate application. The preferred solvents used are aliphatic ketones, ethers and esters, and also any mixtures thereof. Particularly preferred are alkylene glycol monoalkyl ethers, such as, for example, ethylcellosolve, ethylene glycol monobutyl ether, methylcellosolve and 1-methoxy-2-propanol, alkylene glycol alkyl ether-esters such as, for example, methylcellosolve acetate, ethylcellosolve acetate, propylene glycol methyl ether-acetate and propylene glycol ethyl ether-acetate, ketones such as, for example, cyclohexanone, cyclopentanone and butanone, as well as acetates such as butyl acetate, and aromatics such as toluene and xylene. The selection of the appropriate solvents or mixtures thereof depends on the choice of the particular phenolic polymer and of the photosensitive component.

In the method according to the invention for producing relief patterns, a radiation-sensitive recording layer, which contains the radiation-sensitive mixture according to the invention, is exposed imagewise in a dosage such that the solubility of the exposed areas in aqueous-alkaline solvents increases and these irradiated areas can then be selectively removed by the alkaline developer. A positive image is obtained in this way.

Likewise, development with organic solvents such as toluene or anisole is also possible. The unexposed areas show a more pronounced lipophilic character and are therefore removed. This gives a negative image.

Depending on the choice of the developing methods, the radiation-sensitive mixture according to the invention is positive-working or negative-working. It is particularly suitable as a photoresist for producing relief structures or semiconductor components.

The photoresist solutions containing the radiation-sensitive mixture according to the invention are in general applied in layers of 0.1 to 5 μm, preferably 0.5 to 1.5 μm, to suitable substrates, for example superficially oxidized silicon wafers, by spin-coating, dried (e.g. at temperatures between 70 and 130° C.) and exposed imagewise through a photomask to a suitable light source. Suitable light sources are especially shortwave UV rays (deep UV) having wavelengths between 200 and 400 nm. Excimer lasers are particularly suitable light sources.

After the imagewise exposure, development is carried out, if appropriate, after a short post-bake at temperatures of up to 150° C., using conventional aqueous-alkaline developer solutions, in general at a pH between 12 and 14, the exposed areas being washed out leaving a positive image. The resolution is within the sub-half micron region. The exposure energy required for the radiation-sensitive mixture according to the invention is in general between 5 and 200 mJ/cm$^2$ at a layer thickness of 1 $\mu$m. As mentioned previously, a negative image can be performed by selecting an appropriate organic solvent developer.

The developed resist structures are post-hardened if necessary. This may be done in any known manner and is in general effected by heating the resist structure on a hotplate up to a temperature below the flow temperature and then exposing the whole area to UV light from a xenon/mercury vapor lamp (range 200 to 250 nm). As a result of this post-hardening, the resist structures are crosslinked, so that the structures in general are resistant to flow up to temperatures of more than 200° C. The post-hardening can also be effected without an increase in temperature by irradiation with UV light. This applies in particular if high-energy radiation is used.

The radiation-sensitive mixture according to the invention is preferably applied in lithographic processes for the production of integrated circuits or discrete electrical components. The recording material prepared from the mixture here serves as a mask for the subsequent process steps. These steps include, for example, the etching of the layer support, the implantation of ions into the layer support or the deposition of metals or other materials on the layer support. In addition, the radiation-sensitive mixture according to the invention is also suitable for the production of printing plates.

The examples which follow explain the preparation of the monomers, homopolymers and copolymers and the physical and lithographic characterization thereof.

The parts and percentages given in the examples are parts by weight (p.b.w.) and percent by weight (% b.w.), unless otherwise stated.

General Synthesis Instruction 1 for the Preparation of N-(Hydroxybenzyl)-(Meth)Acrylamide Monomers The preparation is carried out analogously to the process indicated in EP-A 0,347,660. In the latter, 129 g (1.0 mol) of N-(methoxymethyl)-(meth)acrylamide (MMMA), 1.0 mol of the phenol chosen for the reaction (cresol, xylenol etc.) and 0.1 mg (0.5 mmol) of phenothiazine are dissolved in 150 ml of ethanol, 1.0 g (10 mmol) of concentrated sulfuric acid is added and the mixture is heated for 7 hours under reflux. After cooling the reaction mixture to 5° C., the colorless product crystallizes out. It is filtered off and dried in a vacuum drying cabinet at 50° C.

Table 1 contains a number of preferred monomers which are prepared according to the general synthesis instruction 1. Further synthesis examples can be taken from CH-A 476,689, DE-C 1,443,912 and EP-A 0,347,660.

TABLE 1

| No. | Monomers or monomer mixtures | Yield [%] |
| --- | --- | --- |
| 1a | N-(4-hydroxy-3,5-dimethylbenzyl)- | 80 |

TABLE 1-continued

| No. | Monomers or monomer mixtures | Yield [%] |
| --- | --- | --- |
|  | methacrylamide |  |
| 1b[a] | (1c:1d ≈ 2:1)[b] | 92 |
| 1c[c] | N-(4-hydroxy-3-methylbenzyl)-methacrylamide | —[d] |
| 1d[c] | N-(2-hydroxy-3-methylbenzyl)-methacrylamide | —[d] |
| 1e[a] | (1f:1g ≈ 1:1)[b] | 96 |
| 1f[c] | N-(4-hydroxybenzyl)-methacrylamide | —[d] |
| 1g[c] | N-(2-hydroxybenzyl)-methacrylamide | —[d] |
| 1h | N-(3,5-diethyl-4-hydroxybenzyl)-methacrylamide | 72 |
| 1i | N-(2-hydroxy-3,5-dimethylbenzyl)-methacrylamide | 75 |

[a]Prepared with the use of N-(butoxymethyl)-(meth)acrylamide in place of MMMA.
[b]The isomer ratios are determined by integration of the proton signals in the $^1$H-NMR spectra.
[c]The monomers are isolated as pure substances from the corresponding monomer mixtures (1c and 1d from 1b, 1f and 1g from 1e) by means of column chromatography on silica gel [gradient elution with petroleum ether/ethyl acetate mixtures (3:1 → 1:7)].
[d]The isolated quantities agreed with the values expected from the integration of the $^1$H-NMR signals.

General Synthesis Instruction 2 for the Preparation of N-(Hydroxybenzyl)-(Meth)Acrylamide Monomers Protected with Tert.-Butoxycarbonyl Groups .0.1 mg (0.5 mmol) of phenothiazine and 30.0 g (0.22 mol) of potassium carbonate are added to a solution of 0.15 mol of an N-(hydroxybenzyl)-(meth)acrylamide monomer or of a monomer mixture 1 (corresponding to the definition given in Table 1) in 200 ml of dry tetrahydrofuran (THF). A solution of 36.2 g (0.165 mol) of di-tert.-butyl dicarbonate (di-tert.-butyl pyrocarbonate) in 60 ml of dry THF is then added dropwise with stirring within 30 minutes at 5 to 10° C.. After warming to room temperature, stirring is continued for a further 40 hours. The reaction mixture is poured onto 1.5 l of ice-water and extracted with ethyl acetate, the organic phase is dried with sodium sulfate and the solvent is distilled off in vacuo. This gives colorless, highly viscous products which partially crystallize after prolonged standing and are used without further purification for the subsequent polymerization. Some of the N-(hydroxybenzyl)-(meth)acrylamide monomers 2 protected with tert.-butoxycarbonyl groups can be crystallized from isopropyl ether.

Table 2 contains a number of preferred monomers which are prepared according to the general synthesis instruction 2.

TABLE 2

| No. | Monomers or monomer mixtures with tert.-butoxycarbonyl protective groups | Yield [%] |
| --- | --- | --- |
| 2a | N-(4-tert.-butoxycarbonyloxy-3,5-dimethylbenzyl)-methacrylamide | 89 |
| 2b | (2c:2d ≈ 2:1) | 86 |
| 2c | N-(4-tert.-butoxycarbonyloxy-3-methylbenzyl)-methacrylamide | 84 |
| 2d | N-(2-tert.-butoxycarbonyloxy-3-methylbenzyl)-methacrylamide | 71 |
| 2e | (2f:2g ≈ 1:1) | 95 |
| 2f | N-(4-tert.-butoxylcarbonyloxy-benzyl)-methacrylamide | 90 |
| 2g | N-(2-tert.-butoxycarbonyloxy-benzyl)-methacrylamide | 85 |
| 2h | N-(4-tert.-butoxycarbonyloxy-3,5-diethylbenzyl)-methacrylamide | 72 |
| 2i | N-(2-tert.-butoxycarbonyloxy-3,5-dimethylbenzyl)-methacrylamide | 81 |

General Synthesis Instruction 3 for the Preparation of Homopolymers From N-(Tert.-Butoxycarbonyloxybenzyl)Methacrylamides:

20 g (about 60 mmol) of the particular monomer 2 (or monomer mixture 2) protected by tert.-butoxycarbonyl groups are heated with 0.30 g (1.83 mmol) of azobisisobutyronitrile (AIBN) in 100 to 150 ml of dry methyl ethyl ketone (MEK)/THF (1:2) (sometimes the MEK/THF ratio must be varied, or ethanol or N,N-dimethylformamide must be added) for 8 hours under reflux in a nitrogen atmosphere. The polymer is precipitated in petroleum ether and dried to constant weight in a vacuum drying cabinet at 50° C.

The yield is more than 90% in all of the Examples. The weight-average molecular weights $M_w$ are between 18,000 and 24,000 g/mol, whereas the number-average molecular weights $M_n$ were found to be around 13,000 g/mol (determined by gel permeation chromatography).

Some of the preferred homopolymers, which are prepared according to the general synthesis instruction 3, are listed below.

Polymer 3a

Homopolymer of N-(4-tert.-butoxycarbonyloxy-3,5-dimethylbenzyl)-methacrylamide

Polymer 3b

Homopolymer of N-(4-tert.-butoxycarbonyloxybenzyl)-methacrylamide

Polymer 3c

Homopolymer of N-(2-tert.-butoxycarbonyloxybenzyl)-methacrylamide

Polymer 3d

Homopolymer of N-(4-tert.-butoxycarbonyloxy-3-methylbenzyl)-methacrylamide

Polymer 3e

Homopolymer of N-(2-tert.-butoxycarbonyloxy-3-methylbenzyl)-methacrylamide

A large number of different copolymers and higher polymers are also prepared according to the general synthesis instruction 3.

The copolymers 4 are obtained from the monomer mixtures 2b and 2e.

Polymer 4a

1:1 copolymer from the monomer mixture 2e [N-(4-tert.-butoxycarbonyloxybenzyl)-methacrylamide and N-(2-tert.-butoxycarbonyloxybenzyl)-methacrylamide]

Polymer 4b

2:1 copolymer from the monomer mixture 2b [N-(4-tert.-butoxycarbonyloxy-3-methylbenzyl)methacrylamide and N-(2-tert.-butoxycarbonyloxy-3-methylbenzyl)-methacrylamide]

The copolymers 5 are prepared by reacting a mixture of N-(3,5-dimethyl-4-tert.-butoxycarbonyloxybenzyl)-methacrylamide 2a and N-(3,5-dimethyl-4-hydroxybenzyl)methacrylamide 1a in various monomer ratios analogously to the conditions of general synthesis instruction 3.

Polymers 5a to 5d

Copolymers from N- (3,5-dimethyl-4-tert.-butoxycarbonyloxybenzyl)-methacrylamide 2a (x) and N- (3,5-dimethyl-4-hydroxybenzyl)-methacrylamide 1a (y).

Polymer 5a:x:y=80:20
Polymer 5b:x:y=60:40
Polymer 5c:x:y=40:60
Polymer 5d:x:y=20:80

The copolymers 6 are prepared by reacting a mixture of N-(4-tert.-butoxycarbonyloxy-3,5-dimethylbenzyl)-methacrylamide 2a and maleimide in various monomer ratios analogously to the conditions of general synthesis instruction 3.

Polymers 6a to 6e

Copolymers from N- (3,5-dimethyl-4-tert.-butoxycarbonyloxybenzyl)-methacrylamide 2a (x) and maleimide (y).

Polymer 6a:x:y=90:10
Polymer 6b:x:y=80:20
Polymer 6c:x:y=70:30
Polymer 6d:x:y=60:40
Polymer 6e:x:y=50:50

Polymers 7 and 8 are prepared by reacting a monomer mixture of 1b and 2b (polymers 7) or a monomer mixture of 1e and 2e (polymer 8) respectively in various mixing ratios analogously to the conditions of general synthesis instruction 3.

Polymers 7a to 7d

Polymers from the monomer mixture 1b [N-(4-hydroxy-3-methylbenzyl)-methacrylamide and N-(2-hydroxy-3-methylbenzyl)-methacrylamide$\approx$2:1] (x) and the monomer mixture 2b [N-(4-tert.-butoxycarbonyloxy-3-methylbenzyl)-methacrylamide and N-(2-tert.-butoxycarbonyloxy-3-methylbenzyl)-methacrylamide$\approx$2:1] (y).

Polymer 7a:x:y=10:90
Polymer 7b:x:y=20:80
Polymer 7c:x:y=30:70
Polymer 7d:x:y=40:60

Polymers 8a to 8d

Polymers from the monomer mixture 1e [N-(4-hydroxybenzyl)-methacrylamide and N-(2-hydroxybenzyl)methacrylamide$\approx$1:1] (x) and the monomer mixture 2e [N-(4-tert.-butoxycarbonyloxybenzyl)-methacrylamide and N-(2-tert.-butoxycarbonyloxybenzyl)-methacrylamide$\approx$1:1 ] (y).

Polymer 8a:x:y=10:90
Polymer 8 b:x:y=20:80
Polymer 8c:x:y=30:70
Polymer 8d:x:y=40:60

It is found here that the amide functional group present in the polymer is sufficient to achieve good adhesion properties.

The following Application Examples 1 to 5 demonstrate the suitability of the mixture according to the invention for recording materials in microlithography. The 1-sulfonyloxy-2-pyridones used in these Examples and the methods for the preparation thereof are described in German Patent Application P 4,112,967.9, equivalent to U.S. patent application Ser. No. 07/870,920, which is hereby incorporated by reference.

APPLICATION EXAMPLE 1

A solution of a radiation-sensitive mixture is prepared, containing

- 2.5 p.b.w. of copolymer 6c, prepared from 70% of N-(4-tert.-butoxycarbonyloxy-3,5-dimethylbenzyl)-methacrylamide 2a and 30% of maleimide,
- 0.075 p.b.w. of 4-methyl-6-styryl-1-trifluoromethanesulfonyloxy-2-pyridone and
- 7.5 p.b.w. of propylene glycol monomethyl etheracetate.

2.0 ml of this solution are filtered through a filter of 0.2 μm pore diameter and applied to a silicon wafer coated with hexamethyldisilazane as an adhesion promoter. The spinning speed is here selected such that a layer thickness of about 1 μm is obtained after 40 seconds. The wafer is dried on a hotplate at 100° C. for 60 seconds, then brought into contact with an imagewise structured test mask and irradiated with radiation of 365 nm (65 mJ/cm$^2$) using a xenon/mercury vapor lamp and an interposed interference filter. The exposed wafer is then subjected for 1 minute to a post-exposure bake at 80° C. and developed for 75 seconds using an 0.05 N aqueous tetramethylammonium hydroxide solution. Structures of 0.60 μm (line/space) are resolved.

APPLICATION EXAMPLE 2

A solution of a radiation-sensitive mixture is prepared, containing

- 2.5 p. b.w. of copolymer 5c, prepared from 40% of N-(4-tert.-butoxycarbonyloxy-3,5-dimethylbenzyl)-methacrylamide 2a and 60% of N-(4-hydroxy-3,5-dimethylbenzyl)-methacrylamide 1a,
- 0.075 p.b.w. of 4-methyl-6-styryl-1-trifluoromethanesulfonyloxy-2-pyridone and
- 7.5 p.b.w. of propylene glycol monomethyl etheracetate.

2.0 ml of this solution are filtered through a filter of 0.2 μm pore diameter and applied to a silicon wafer coated with hexamethyldisilazane as adhesion promoter. The spinning speed is here selected such that a layer thickness of about 1 μm is obtained after 40 seconds. The wafer is dried on a hotplate at 100° C. for 60 seconds, then brought into contact with an imagewise structured test mask and irradiated with radiation of 365 nm (65 mJ/cm$^2$) using a xenon/mercury vapor lamp and an interposed interference filter. The exposed wafer is then subjected for 1 minute to a post-exposure bake at 80° C. and developed for 75 seconds, using an 0.09 N aqueous tetramethylammonium hydroxide solution. Structures of 0.70 μm (line/space) are resolved.

APPLICATION EXAMPLE 3

A solution of a radiation-sensitive mixture is prepared, containing

- 2.5 p.b.w. of the 2:1 copolymer 4b, prepared from monomer mixture 2b [65% of N-(4-tert.-butoxycarbonyloxy-3-methylbenzyl)-methacrylamide and 35% of N-(2-tert.-butoxycarbonyloxy-3-methylbenzyl)-methacrylamide,
- 0.075 p.b.w. of triphenylsulfonium trifluoromethanesulfonate and
- 7.5 p.b.w. of propylene glycol monomethyl etheracetate.

2.0 ml of this solution are filtered through a filter of 0.2 μm pore diameter and applied to a silicon wafer coated with hexamethyldisilazane as adhesion promoter. The spinning speed is here selected such that a layer thickness of about 1 μm is obtained after 40 seconds. The wafer is dried on a hotplate at 100° C. for 60 seconds, then brought into contact with an imagewise structured test mask and irradiated with radiation of 365 nm (60 mJ/cm$^2$) using a xenon/mercury vapor lamp and an interposed interference filter. The exposed wafer is then subjected for 1 minute to a post-exposure bake at 85° C. and developed for 45 seconds, using an 0.135 N aqueous tetramethylammonium hydroxide solution. Structures of 0.60 μm (line/space) are resolved.

APPLICATION EXAMPLE 4

A solution of a radiation-sensitive mixture is prepared from

- 2.5 p.b.w. of polymer 8a corresponding to the composition indicated above,
- 0.09 p.b.w. of triphenylsulfonium hexafluoroantimonate and
- 7.5 p.b.w. of propylene glycol monomethyl etheracetate.

2.0 ml of this solution are filtered through a filter of 0.2 μm pore diameter and applied to a silicon wafer coated with hexamethyldisilazane as adhesion promoter. The spinning speed is here selected such that a homogeneous layer of a layer thickness of about 1 μm is obtained after 40 seconds. The wafer is dried on a hotplate at 100° C. for 60 seconds, then brought into contact with an imagewise structured test mask and irradiated with radiation of 248 nm (70 mJ/cm$^2$) using a KrF-excimer laser. The wafer is then held for 1 minute at 90° C. and developed for 120 seconds with anisole. Structures of 0.70 μm (line/space) are resolved.

APPLICATION EXAMPLE 5

A solution of a radiation-sensitive mixture is prepared from

- 2.5 p.b.w. of polymer 7b corresponding to the composition indicated above,
- 0.075 p.b.w. of triphenylsulfonium trifluoromethanesulfonate and
- 7.5 p.b.w. of propylene glycol monomethyl etheracetate.

2.0 ml of this solution are filtered through a filter of 0.2 μm pore diameter and applied to a silicon wafer coated with hexamethyldisilazane as adhesion promoter. The spinning speed is here selected such that a homogeneous layer of a layer thickness of about 1 μm is obtained after 40 seconds. The wafer is dried on a hotplate at 100° C. for 60 seconds, then brought into contact with an imagewise structured test mask and irradiated with radiation of 240 nm wavelength (55 mJ/cm$^2$) using a KrF-excimer laser. The exposed wafer is then subjected for 1 minute to a post-exposure bake at 85° C. and developed for 45 seconds, using a 0.135 N aqueous tetramethylammonium hydroxide solution. Structures of 0.55 μm (line/space) are resolved.

What is claimed is:

1. A polymer comprising units of the formula (I)

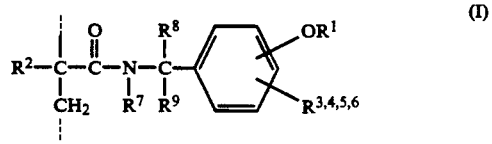

in which

R$^1$ is an acid-labile protecting group, $R^2$ is $(C_1-C_4)$-alkyl, halogenated-$(C_1-C_4)$-alkyl, halogen, CN, or hydrogen, $R^{3,4,5,6}$ independently of one another are aliphatic, araliphatic or aromatic radicals each independently having 1 to 20 carbon atoms and each being unsubstituted or halogen substituted, halogen, hydroxyl or hydrogen, $R^7$ is a hydrogen atom or a $(C_1-C_4)$-alkyl group, and $R^8$ and $R^9$ are identical or different and are hydrogen, a $(C_1-C_6)$-alkyl group or a $(C_6-C_{10})$-aryl group.

2. A polymer as claimed in claim 1, wherein $R^1$ is a benzyl, trialkylsilanyl, alkoxycarbonyl, tetrahydropyranyl or tetrahydrofuranyl group, $R^2$ is hydrogen or a methyl group, $R^3$ to $R^6$ independently of one another are each hydrogen, a hydroxyl group or a methyl group, and $R^7$ to $R^9$ are hydrogen.

3. A polymer as claimed in claim 2, which comprises at least 10 mol % of units of formula (I).

4. A polymer as claimed in claim 1, wherein the group $OR^1$ is a tert.-butoxycarbonyl group and $OR^1$ is in the ortho- or para-position relative to the $-CR^8R^9$ group.

5. A polymer as claimed in claim 1 which comprises at least 10 mol % of units of the formula I, the remainder being comprised of polymerized units of other vinyl monomers.

6. A polymer as claimed in claim 5, which is a copolymer further containing polymerized units of at least one monomer selected from the group consisting of monomers of formula (III)

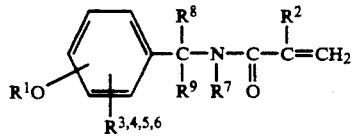

(III)

in which $R^2$ is $(C_1-C_4)$alkyl, halogenated-$(C_1-C_4)$-alkyl, halogen, CN, or hydrogen, $R^{3,4,5,6}$ independently of one another are an unsubstituted or halogen-substituted aliphatic, araliphatic or aromatic radical having 1 to 20 carbon atoms, halogen, hydroxy or hydrogen, $R^7$ is a hydrogen atom or a $(C_1-C_4)$-alkyl group, $R^8$ and $R^9$ are identical or different and are hydrogen, a $(C_1-C_6)$-alkyl group or a $(C_6-C_{10})$-aryl group, and $R^1$ is H or a non-acid-cleavable group, maleimide, methacrylic acid, an ester or amide of (meth)acrylic acid or a vinyl ether.

7. A polymer as claimed in claim 6, which contains units from monomers of formula (III).

8. A polymer as claimed in claim 1, which is a homopolymer.

9. A polymer as claimed in claim 1, which additionally comprises silicon-containing units.

10. A polymer as claimed in claim 9, wherein the silicon-containing units are formed by polymerizing one or more monomers selected from the group consisting of trialkyl-vinyl silanes and trialkylsilanyl acrylates and methacrylates.

11. A polymer as claimed in claim 1, which has a number average molecular weight of 2,000 to 100,000.

12. A polymer as claimed in claim 11, wherein said molecular weight is between 5,000 and 40,000 g/mol.

13. A polymer as claimed in claim 1 which is a copolymer of a plurality of different units each having formula (I).

14. A polymer as claimed in claim 1, which consists essentially of one or more units of the formula (I).

15. A polymer as claimed in claim 1, which consists of one or more units of the formula (I).

16. A polymer as claimed in claim 1, which further contains polymerized units of other vinyl monomers.

17. A polymer as claimed in claim 16, wherein the other vinyl monomers are selected from one or more of the group consisting of methacrylic acid and esters or amides of methacrylic acid.

18. A polymer as claimed in claim 1, which further contains polymerized maleimide units.

19. A polymer as claimed in claim 1, which further contains polymerized units of one or more of styrene, substituted styrenes, vinyl ethers, and vinyl esters.

20. A polymer as claimed in claim 1, wherein OR is a tert.-butoxycarbonyloxy group.

21. A polymer as claimed in claim 1, which comprises at least 10 mol % of units of formula (I).

* * * * *